(12) United States Patent
Forse et al.

(10) Patent No.: US 6,172,106 B1
(45) Date of Patent: Jan. 9, 2001

(54) SESAMOL INHIBITION OF Δ-5-DESATURASE ACTIVITY AND USES THEREFOR

(76) Inventors: R. Armour Forse, 50 Fisher Ave., Brookline, MA (US) 02146; Sambasiva R. Chavali, 352 Riverway #2, Boston, MA (US) 02115

( * ) Notice: Under 35 U.S.C. 154(b), the term of this patent shall be extended for 0 days.

(21) Appl. No.: 09/429,420

(22) Filed: Oct. 28, 1999

Related U.S. Application Data

(62) Division of application No. 09/020,550, filed on Feb. 9, 1998.

(51) Int. Cl.⁷ ..................................................... A61K 31/36
(52) U.S. Cl. .............................................................. 514/464
(58) Field of Search ............................................... 514/464

(56) References Cited

U.S. PATENT DOCUMENTS

| | | | |
|---|---|---|---|
| 4,335,113 | 6/1982 | Combier et al. | 424/180 |
| 5,397,778 | * 3/1995 | Forse et al. | 514/198 |
| 5,594,021 | 1/1997 | Chan et al. | 514/378 |

FOREIGN PATENT DOCUMENTS

| | | |
|---|---|---|
| 0 165 810 A2 | 12/1985 | (EP) . |
| WO 92/01682 | 2/1992 | (WO) . |
| WO 95/22971 | 8/1995 | (WO) . |
| WO 97/25045 | 7/1997 | (WO) . |
| WO 97/25321 | 7/1997 | (WO) . |

OTHER PUBLICATIONS

Naganuma, H., and Kawahara, Y., "Sensitive Fluorescence Labelling for Analysis of Carboxylic Acids with 4–Bromomethyl–6,7–Methylenedioxycouma–RIN", *Journal of Chromatography*, 478:149–158 (1989).

Shimizu et al., Lipids, 26(7), 512–516, 1991.*

* cited by examiner

*Primary Examiner*—Phyllis G. Spivack
(74) *Attorney, Agent, or Firm*—Hamilton, Brook, Smith & Reynolds, P.C.

(57) ABSTRACT

Methods for inhibiting Δ-5-desaturase activity, for inhibiting arachidonic acid metabolism, for inhibiting $PGE_2$ levels and for inhibiting $PLA_2$ activity comprising administering sesamol are disclosed.

5 Claims, 3 Drawing Sheets

Linoleic acid (18:2 ω6 -9,12)

↓            *Δ-6 desaturation*

γ-Linolenic acid (18:3 ω6 -6,9,12)

↓            *2 carbon chain elongation*

Dihomo-γ-Linolenic acid (20:3 ω6 -8,11,14)

↓            *Δ-5 desaturation*

Arachidonic acid (20:4 ω6 -5,8,11,14)

↓            *2-carbon chain elongation*

Adrenic acid (22:4 ω6 -7,10,13,16)

↓            *Δ-4 desaturation*

Docosapentaenoic acid (22:5 ω6 -4.7,10,13,16)

Figure 3

SESAMOL INHIBITION OF Δ-5-DESATURASE ACTIVITY AND USES THEREFOR

RELATED APPLICATION

This application is a Divisional of co-pending U.S. application Ser. No. 09/020,550 filed Feb. 9, 1998, the entire teachings of which are incorporated herein by reference.

BACKGROUND OF THE INVENTION

Dietary polyunsaturated fatty acids (PUFA) play a major role in the regulation of immune responses during infection and inflammation. Linoleic acid (LA:18:2ω6) is the precursor for the formation of arachidonic acid which is metabolized to proinflammatory mediators such as prostaglandins (PG)$E_2$ and thromboxane (Tx)$A_2$. Other polyunsaturated fatty acids such as α-linolenic acid (18:3ω6) and γlinolenic acid (18:3ω6) are precursors for the formation of eicosapentaenoic acid (EPA: 20:5ω3) and dihomo-γ-linolenic acid (DGLA: 20:3ω6), respectively, both of which displace arachidonic acid (20:4ω6), reduce the production of $PGE_2$ and also form mediators such as $PGE_3$ and $PGE_1$ which are less inflammatory. Thus, dietary fats rich in γ-linolenic acid, α-linolenic acid, or EPA have been employed to modulate some of the inflammatory responses in experimental animal models (Carrick et al., *Shock* 2:421–426 (1994); Yacoob and Calder, *Cell Immunol* 163:120–128 (1995)) and in clinical trials (Espersen et al., *Clin Rheumatol* ll:393–395 (1992); Engler et al., *J Hyperien* 10(1):197–204 (1992); Harrobin, *Rev Contem Pharmacol. Ther.* 1:1–45 (1990)).

Recently, it has been demonstrated that in animals fed sesame seed oil (SSO), an increased survival in mice exposed to a lethal dose of LPS is associated with a substantial increase in the accumulation of dihomo-γ-linolenic acid (Chavali et al., *Int Arch Allergy Immunol* 114:153–160 (1997)). Moreover, the experimental data suggest that these beneficial effects are attributed to the lignans in the non-fat portion of the oil. These lignans, including sesamin, episesamin, sesaminol and sesamolin but not sesamol, inhibit the activity of Δ-5 desaturase enzyme in vitro (Shimizu et al., *Lipids* 26:512–516 (1991)). Unlike sesamol (3,4-methylenedioxyphenol), the other lignans are dimeric compounds and have in common a methylene-bridged 3,4-dihydroxyphenol moiety (FIGS. 1A and 1B). Further, data (Shimizu et al., *Lipids* 26:512–516 (1991); Fujiyama et al., *J Nutr Sci Vitaminol* 41:217–225 (1995)) suggest that sesamin inhibits the Δ-5 desaturase activity of ω6 polyunsaturated fatty acids, resulting in an accumulation of dihomo-γ-linolenic acid. In mice fed sesamin, the LPS-induced production of $PGE_2$, IL-10 and IL-6 was lower and that of TNF-α was higher, while these levels are unaffected in SSO fed animals (Chavali et al., *Int Arch Allergy Immunol* 114:153–160 (1997)).

SUMMARY OF THE INVENTION

As described herein, the effects of consumption of sesamol-supplemented safflower oil (SO) diet (providing linoleic acid, an essential fatty acid) on the fatty acid composition and the endotoxin-induced production of eicosanoids as well as cytokines in mice, were investigated. The fatty acid composition (mean±s.d. mol. %) of liver membrane phospholipids and the levels of endotoxin-induced prostaglandin (PG) $E_2$, interleukin (IL)-6, IL-10, IL-12 and tumor necrosis factor (TNF)-α were determined in mice fed diets supplemented with safflower oil (5%) and sesamol (1%). The levels of dihomo-γ-linolenic acid (DGLA; 20:3ω6) were markedly higher (p<0.05) in the livers from mice fed sesamol supplemented SO diets (1.6±0.1) compared to the controls (1.4±0.1). In contrast, the levels of docosapentaenoic acid (22:5ω6) were significantly lower in animals fed sesamol (1.4±0.1) compared to the controls (2.5±0.4). These data suggest that sesamol or its metabolite can inhibit the in vivo Δ-5 desaturation of ω6 fatty acids.

Further, in animals fed sesamol-supplemented SO diets, the levels of $PGE_2$ (228±41 pg/ml) were markedly lower (p<0.05) compared to those fed SO diet alone (1,355±188 pg/ml). In the group of animals maintained on sesamol supplemented diets, the plasma levels of IL-6 (63±11 ng/ml) were significantly lower compared to those fed SO diet alone (143±22 ng/ml). The concentrations of TNF-α and IL-10 did not differ significantly between the two dietary groups. In mice fed sesamol-supplemented diets, even in the absence of any differences in the amounts of arachidonic acid, a marked reduction of $PGE_2$ levels suggest that the observed anti-inflammatory effects could result from the ability of sesamol to inhibit or decrease the activity of phospholipase $A_2$ ($PLA_2$) responsible for the release of arachidonic acid from membrane phospholipids.

The invention pertains to compositions comprising sesamol in an amount effective to treat inflammation. In particular embodiments, the composition is a dietary supplement or nutritional solution, such as a dietary supplement or nutritional solution suitable for enteral or parenteral administration. In one embodiment of the invention, the sesamol of the composition is essentially purified. In other embodiments, the composition further comprises essential fatty acids and/or essential vitamins and minerals.

The invention further relates to a dietary supplement or medical food comprising an effective amount of sesamol. For example, the dietary supplement or medical food can be selected from the group consisting of nutritional beverage, baked good (cookie, brownie, fudge, cake, bread, biscuit and cracker), pudding, confection, snack food, ice cream, frozen confection, and non-baked, extruded food product such as a bar.

The invention also pertains to a method of inhibiting inflammation in a mammal comprising administering a composition comprising an effective amount of sesamol to a mammal in need thereof. In one embodiment, the composition to be administered is a dietary supplement or nutritional solution, such as one which is suitable for enteral or parenteral administration. In another embodiment, the composition further comprises essential fatty acids and/or essential vitamins and minerals. The composition can be administered enterally or parenterally.

The invention also pertains to a method of inhibiting inflammation in a mammal comprising administering a composition comprising an effective amount of a sesamol metabolite to a mammal in need thereof, as well as to compositions comprising a sesamol metabolite in an amount effective to treat inflammation.

The invention also pertains to a method of inhibiting Δ-5-desaturase activity in a mammal comprising administering to the mammal a composition comprising an effective amount of sesamol or a sesamol metabolite.

The invention further relates to a method of inhibiting arachidonic acid metabolism in a mammal comprising administering to the mammal a composition comprising an effective amount of sesamol or a sesamol metabolite. Inhibition of arachidonic acid metabolism results in inhibition of the formation of arachidonic acid metabolites, such as $PGE_2$ and thromboxane (Tx)$A_2$.

The invention further relates to a method of inhibiting the level of $PGE_2$ and $TxA_2$ in a mammal comprising administering to the mammal a composition comprising an effective amount of sesamol or a sesamol metabolite.

The invention also relates to a method of inhibiting the activity of $PLA_2$ in a mammal comprising administering to the mammal a composition comprising an effective amount of sesamol or a sesamol metabolite.

Sesamol has several benefits and advantages for the health of mammals to which it is administered. In general, consumption of sesamol-supplemented diets could improve the functions of vital organs such as heart, lungs, liver and kidneys. The levels of TNF, a proinflammatory mediator, are not elevated in mice fed sesamol in contrast to TNF levels with other anti-inflammatory drugs; therefore, use of sesamol as an anti-inflammatory agent does not induce the undesirable side effects induced by many other anti-inflammatory agents. Further, because it is available naturally in sesame oil, sesamol can be used as a dietary supplement providing beneficial effects to the host. Proinflammatory mediators such as $PGE_2$ and IL-6 are also associated with increased mortality of patients with cancer/neoplasia and of those with sepsis and septic shock. The ability of sesamol to decrease the levels of these mediators without affecting the levels of TNF can positively impact therapy regimens.

BRIEF DESCRIPTION OF THE DRAWINGS

FIG. 3 is a schematic diagram depicting the desaturation and chain elongation processes of linoleic acid, the precursor for the formation of arachidonic acid.

DETAILED DESCRIPTION OF THE INVENTION

Figure 1A:
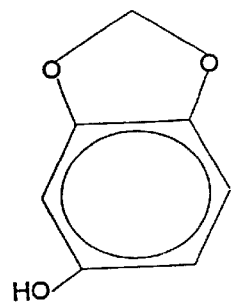
FIGS. 1A and 1B are diagrams of the chemical structures of sesamol (FIG. 1A) and sesamin (FIG. 1B).

As illustrated in FIG. 3, linoleic acid (LA; 18:2ω6-9,12) is desaturated at the Δ-6 carbon to form γ-linolenic acid (18:3ω6 -6,9,12), which is elongated to dihomo-γ-linolenic acid (20:3ω6-8,11,14). Following desaturation at the Δ-5 carbon, dihomo-γ-linolenic acid forms arachidonic acid (20:4ω6 -5,8,11,14) that is elongated to form adrenic acid (22:4ω6 -7,10,13,16) which, in turn, is desaturated at Δ-4 giving rise to docosapentaenoic acid (22:5ω6 -4,7,10,13,16) (Holman, *Prog Lipid Res* 25:29–39 (1986)). Docosapentaenoic acid and intermediates in this pathway can modulate immune and inflammatory responses.

As described herein, a decrease in the tissue levels of ω6 docosapentaenoic acid was associated with a concomitant increase in dihomo-γ-linolenic acid in animals maintained on sesamol-supplemented SO diet. In the absence of detectable levels of adrenic acid (22:4ω6), and due to the fact that the levels of arachidonic acid were unchanged, a reduction in the levels of docosapentaenoic acid in animals fed sesamol-supplemented SO diets (Table 1) could result from the ability of sesamol to inhibit Δ-5 desaturase activity resulting in the accumulation of dihomo-γ-linolenic acid (Holman, *Prog Lipid Res* 25:29–39 (1986); Jeffcoat, *Essays in Biochem* 15:1–36 (1979)). These data suggest that the inhibition of Δ-5 desaturation of ω6 polyunsaturated fatty acids results from a metabolite of sesamol, as sesamol does not inhibit Δ-5 desaturase activity in vitro according to Shimizu et al. (*Lipids* 26:512–516 (1991)).

TABLE 1

Effects of sesamol on the fatty acid composition of liver membrane phospholipids from mice fed sesamol-supplemented safflower oil diets for 2 weeks.

|  | SAFFLOWER OIL (SO) | SO + SESAMOL (SO+) |
|---|---|---|
| Palmitic acid (16:0) | 19.4 ± 0.7 | 19.5 ± 1.4 |
| Stearic acid (18:0) | 18.6 ± 1.3 | 19.2 ± 1.7 |
| Oleic acid (18:1ω9) | 8.0 ± 0.7 | 8.2 ± 1.1 |
| Vaccenic acid (18:1ω7) | 2.4 ± 0.5 | 2.6 ± 0.4 |
| Linolenic acid (18:2ω6) | 13.2 ± 0.6 | 13.6 ± 0.7 |
| DGLA (20:3ω6) | 1.4 ± 0.1 | 1.6 ± 0.1[a] |
| Arachidonic acid (20:4ω6) | 25.7 ± 1.1 | 24.9 ± 0.9 |
| Docosapentaenoic acid (22:5ω6) | 2.5 ± 0.4 | 1.4 ± 0.1[a] |
| Docosahexaenoic acid (22:6ω3) | 9.7 ± 0.6 | 9.5 ± 0.4 |
| Δ-5 desaturation (20:4ω6/20:3) | 18.0 ± 1.7 | 15.6 ± 1.5[a] |

[a]vs. with SO diets without sesamol.

Table 1 shows the results of experiments in which groups of animals (n=8) were maintained on diets containing 5 wt % safflower oil (SO) without or with supplementation of 1% sesamol (+) for 2 weeks. The phospholipid fatty acid composition of the livers were determined, and the data represent mean mole percents of the total fatty acids (±s.d.). The levels of significance between the groups were determined using an unpaired student's t-test (p,0.05).

TABLE 2

Effects of sesamol on the circulating levels of LPS-induced production of cytokines in mice fed sesamol-supplemented safflower oil diets for 2 weeks.

| CYTOKINES | SAFFLOWER OIL (SO) | SO + SESAMOL |
|---|---|---|
| Tumor Necrosis Factor (TNF)-α (pg/ml) | 3,042 ± 428 | 2,931 ± 461 |
| Interleukin (IL)-6 (ng/ml) | 143 ± 22 | 63 ± 11* |
| IL-10 (pg/ml) | 262 ± 15 | 236 ± 20 |
| IL-12 (pg/ml) | 6,355 ± 482 | 6,620 ± 646 |

Table 2 shows the results of experiments which were carried out as detailed in the assessment of circulating levels of prostaglandin (PG) $E_2$. Data represent the levels of IL-6 (means±s.e.) in plasma samples obtained at 1 hour for TNF-α, and at 3 hours for IL-6, IL-10, and IL-12 following LPS exposure. The levels of significance (*P<0.05) in the differences between the two groups were determined using a student's t-test.

As described herein, a decrease in the plasma levels of $PGE_{1+2}$ was associated with an increase of dihomo-γ-linolenic acid in mice fed a sesamol-supplemented SO diet (Table 1). Dihomo-γ-linolenic acid can displace arachidonic acid, compete with it in binding to cyclooxygenase, and consequently, reduce the levels of proinflammatory dienoic eicosanoids and also increase the formation of less inflammatory 1-series PG (Harrobin, *Rev Contem Pharmacolther* 1:1–45 (1990); Weaver and Holob, *Prog Food Nutr Sci* 12:111–150 (1988); Holman, *Prog Lipid Res* 25:29–39 (1986)). Despite the lack of differences in the tissue levels of arachidonic acid (Table 1), a decrease in the plasma levels of $PGE_{1+2}$ in mice fed sesamol-supplemented SO diet suggests that a decline in the levels of PGs could result from the ability of sesamol or its metabolites to decrease the activity of $PLA_2$, responsible for arachidonic acid release from membrane phospholipids.

Figure 2:
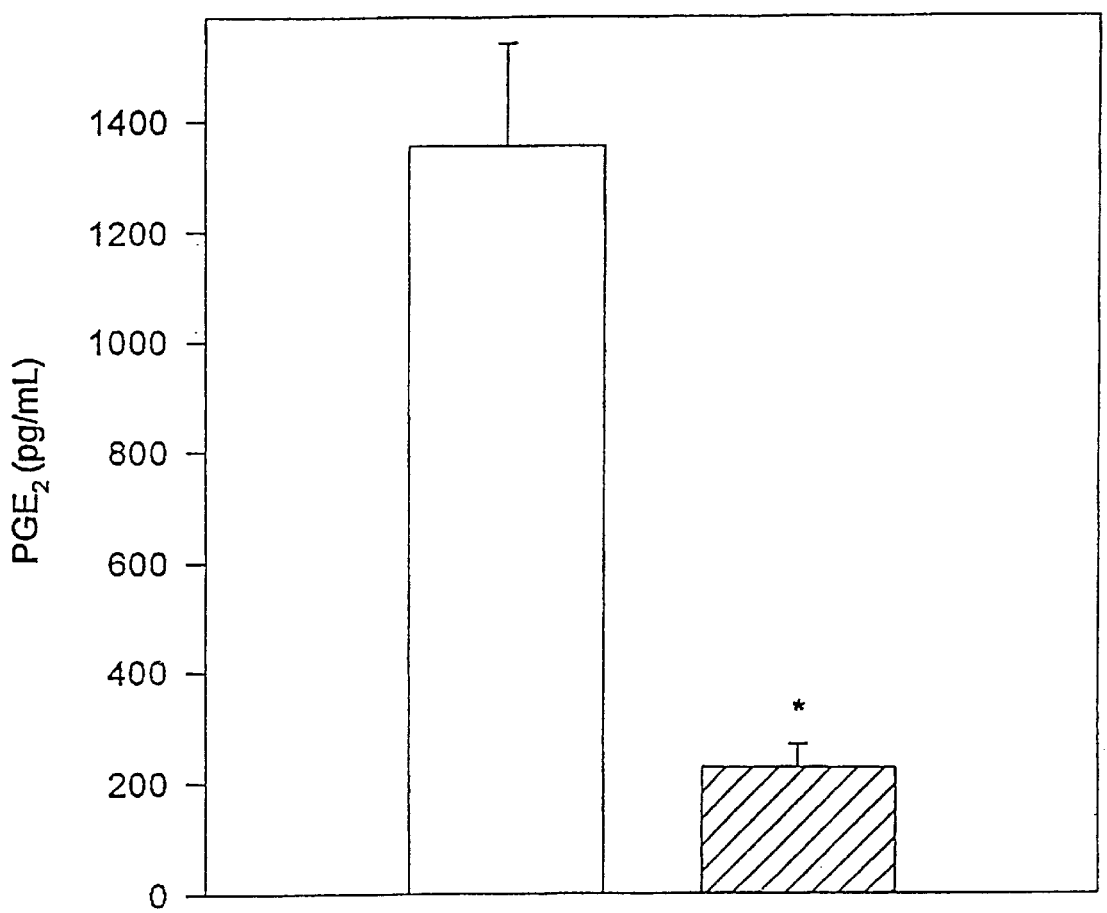
FIG. 2 is a graph showing the effects of feeding sesamol-supplemented diets on the circulating levels of prostaglandin (PG) $E_2$ in mice. Mice were fed diets containing safflower oil (SO) without (open bar) or with (+; hatched bar) 1% sesamol for 3 weeks. The levels of significance in the differences was determined using a student t-test (*=P<0.05 compared to SO fed animals).

The ability of nutrients to modulate the production of cytokines (Carrick et al., *Shock* 2:421–426 (1994); Yacoob and Calder, *Cell Immunol* 163:120–128 (1995)) associated with severity of sepsis (Lowry, *Arch Surg* 128:1223–1241 (1993)) have been explored (Chavali et al., *Int Arch Allergy Immunol* 114:153–160 (1997); Utsunomiya et al., *Biochim. Biophys. Acta.* 1214:333–339 (1994)), and the results are often contradictory. IL-6 is a major contributor to the toxic effects of LPS and TNF-α (Damas et al., *Ann Surg* 215:356–362 (1991)), and the treatment of mice with anti-IL-6 monoclonal antibody decreases mortality resulting from a subsequent challenge with LPS or TNF-α (Stames et al., *J Immunol* 145:4185–4191 (1990)). These data suggest that IL-6 plays a critical role during infection and inflammation. An increase in the levels of $PGE_2$ could cause an increase in the circulating levels of IL-6 in mice consuming SO diets as was demonstrated elsewhere (Leal-Berumen et al., *J Immunol* 154: 4759 (1995); Bella et al., *Prostaglandins Leukotrienes and Essential Fatty Acids* 56:177–184 (1997)). Consistent with these data, a decrease in the levels of $PGE_2$ (FIG. 2) was associated with a significant reduction in the levels of IL-6 in mammals fed sesamol-supplemented SO diets.

An increase in the production of TNF-α is associated with a decrease in the levels of $PGE_2$ as shown in mice fed sesamin, and also in the supernatants of cell cultures in the presence of the PG synthesis inhibitor, indomethacin (Utsunomiya et al., *Eu J Pharmacol* 252:213–218 (1994); Tsuboi et al., *Cytokine* 7:372–379 (1995)). As with sesamin diets, consumption of sesamol diet in the present study inhibited Δ-5 desaturation of ω6 polyunsaturated fatty acids, and also decreased the levels $PGE_2$, a proinflammatory mediator associated with infection and inflammation. In the group of animals maintained on sesamol-supplemented diets, the plasma levels of IL-6 (63±11 ng/ml) were significantly lower compared to those fed an SO diet alone (143±22 ng/ml). The levels of IL-10 and TNF-α were unaffected in mice fed sesamol-supplemented diets. In contrast, the levels of IL-10, an anti-inflammatory mediator were decreased, and those of IL-6 and of TNF-α, both proinflammatory mediators, were elevated in mice fed sesamin diets. The weights of livers were unaffected in mice consuming sesamol-supplemented diets, and they were markedly higher in rats fed sesamin-containing diets (Fujiyama et al., *J Nutr Sci Vitaminol* 41:217–225 (1995)). These data suggest that sesamol or its metabolites, unlike sesamin, did not elevate TNF-α, or the weights of the livers under these experimental conditions.

Thus, the invention encompasses compositions comprising sesamol or a sesamol metabolite in an amount effective to treat (i.e., inhibit) inflammation, such as inflammation associated with infection. As used herein, treatment or inhibition encompasses reduction in symptomology associated with infection or inflammation, including complete resolution of the inflamed condition. Treatment and inhibition are also intended to include reduction or minimization of risk of inflammation in a mammal at risk for such symptoms or conditions.

Compositions comprising sesamol or a sesamol metabolite can be in any form suitable for administration to a mammal, including tablet, powder, capsule, liquid, injectable and suppository forms. In preferred embodiments, the composition is a dietary supplement or a nutritional solution.

For example, the dietary supplement can contain essential fatty acids and/or essential vitamins and minerals in addition to sesamol or a sesamol metabolite. The dietary supplement can be provided in a variety of forms, such as nutritional beverages, baked goods (e.g., cookies, brownies, fudge, cake, breads, biscuits, crackers), puddings, confections (i.e., candy), snack foods (e.g., pretzels, chips), ice cream, frozen confections and novelties, or non-baked, extruded foods such as bars.

The dietary supplement can provide optimal nutrition for growth and weight maintenance, and can comprise protein, carbohydrate and fat components, alone or in combination, in addition to an effective amount of sesamol. For example, the carbohydrate sources can include, but are not limited to, one or more of corn syrup, high fructose corn syrup, corn starch, maltodextrin, fructose, lactose, glucose, sucrose, dextrose and maltose. The protein sources can include, but are not limited to, one or more of whey protein, whey protein concentrate, whey powder, egg protein, soy protein, soy protein isolate and caseinate. The fat sources can include, but are not limited to, one or more of dietary fats, coconut oil, peanut oil, safflower oil, canola oil, corn oil, sesame seed oil, fish oil and vegetable oil, as well as structured triglycerides, long-chain triglycerides and medium-chain triglycerides. The dietary supplement can also comprise adjunct ingredients such as emulsifiers (e.g. saponins), preservatives, artificial sweeteners, thickeners, colorings and flavors which improve the palatability, stability, shelf-life and organoleptic properties of the composition. (See U.S. Pat. Nos. 5,674,853 and 5,397,778.)

The nutritional solution can be a parenteral nutritional solution, such as a total parenteral nutritional solution which contains all essential nutrients for health. The composition can also comprise additional components as appropriate. For instance, the sesamol or sesamol metabolite can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions.

As used herein, an effective amount includes an amount sufficient to show statistically significant anti-inflammatory effects. The range of effective amounts will generally be from about 0.1 to about 10 mg/kg body weight of the mammal to be treated. The optimum concentration of the active ingredient(s) in the chosen medium can be determined empirically, according to procedures well known in the art, and will depend on the ultimate pharmaceutical formulation desired. Sesamol or a sesamol metabolite can be present in the composition in a purified form or administered in the form of sesame seed oil, sesame seeds, or sesame extract.

As used herein, sesamol can be in either an isolated or synthetic form; that is, sesamol can be isolated from sesame oil or it can be synthesized chemically. Moreover, the term sesamol is intended to include sesamol metabolites as well as sesamol itself. Sesamol metabolites include any secondary metabolite produced by direct or subsequent metabolism of sesamol; that is, sesamol metabolites include products produced by direct metabolism of sesamol itself (primary metabolites), as well as secondary products produced by further metabolism of the primary metabolites (secondary metabolites). The determination of the metabolite or metabolites responsible for the anti-inflammatory properties of sesamol can be determined by assessing the ability of each sesamol metabolite to inhibit Δ-5-desaturase activity by art recognized methods such as those described herein or by methods such as those described by Shimizu et al. (*Lipids*

26:512–516 (1991)). Sesamol metabolites which are identified as having inhibitory ability in vitro can then be studied to assess the in vivo anti-inflammatory properties of the metabolite by art recognized methods such as those described herein or those described by Shimizu et al. (*Lipids* 26:512–516 (1991)). Metabolic derivatives of compounds which are structurally related to sesamol, such as sesamin, and sesamol dimers and trimers can also be used in the methods described herein.

The invention also relates to methods of treating or inhibiting inflammation by administering a composition comprising an effective amount of sesamol to a mammal in need thereof. Suitable mammals include, but are not limited to, primates (e.g., humans), dogs, cats, cows, horses, pigs and goats. Methods of administering such compositions include, but are not limited to, intradermal, intramuscular, intraperitoneal, intravenous, subcutaneous, oral, suppository and intranasal. Particularly preferred methods of administration are enteral and parenteral administration. Other suitable methods of introduction can also include rechargeable or biodegradable devices and slow release devices. The compositions of this invention can also be administered as part of a combinatorial therapy with other agents, including anti-inflammatory agents and antibiotics.

The methods of the present invention can be used to reduce the incidence or symptomology of inflammation associated with infection by various organisms, as well as to reduce the occurrence or severity of inflammation associated with other conditions. For example, the methods of the present invention are useful to treat conditions such as arthritis, lyme disease, aging, breast cancer, head and neck cancer, common colds and flu and sepsis.

The invention also encompasses methods of inhibiting $\Delta$-5-desaturase activity in a mammal comprising administering to the mammal a composition comprising an effective amount of sesamol or a sesamol metabolite. Inhibition of $\Delta$-5-desaturase activity is intended to include an inhibition or reduction in levels or activities of enzymes responsible for the $\Delta$-5-desaturation of dihomo-$\gamma$-linolenic acid, such as $\Delta$-5-desaturase enzyme. The inhibition of $\alpha$-5-desaturase activity results in an increase in the level of dihomo-$\gamma$-linolenic acid and a decrease in any or all of the compounds for which dihomo-$\gamma$-linolenic acid is a precursor, such as arachidonic acid, adrenic acid and docosapentaenoic acid. The result of $\Delta$-5-desaturase inhibition is a decrease in proinflammatory mediators such as prostaglandins. Thus, the invention also encompasses a method of inhibiting the level of $PGE_2$ in a mammal comprising administering to the mammal a composition comprising an effective amount of sesamol or a sesamol metabolite.

Moreover, even in the absence of effects on arachidonic acid levels, a reduction in $PGE_2$ suggests that sesamol has the ability to inhibit or decrease the level or activity of $PLA_2$, which is responsible for the release of arachidonic acid from membrane phospholipids. Thus, the invention also relates to a method of inhibiting the activity of $PLA_2$ in a mammal comprising administering to the mammal a composition comprising an effective amount of sesamol or a sesamol metabolite.

The following Examples are offered for the purpose of illustrating the present invention and are not to be construed to limit the scope of this invention. The teachings of all references cited herein are hereby incorporated herein by reference.

EXAMPLES

Materials and Methods

Animals: Six 8-week old, inbred, female Balb/c mice (Taconic Farms) were housed in our animal facility with a 12 hour day and 12 hour night cycle. They were allowed free access to drinking water and the experimental diets were fed at dusk, daily, between 4–5 PM. The weights of the body, and of the liver and spleen were determined on days 4, 7 and 14.

Diets: The AIN-76A fat-free powder along with 0.05% t-butyl hydroxy toluene, an antioxidant, was mixed with 5 wt % (10% Kcal) of safflower oil (Oilseeds International Ltd., Fresno, Calif.), partitioned into daily rations packaged in separate whirl-pack bags, flushed with $N_2$, and stored at 4° C. Where indicated, these diets were supplemented with 1 wt % sesamol (Aldrich Chemical Company Inc. Milwaukee, Wis.).

Fatty acid analysis: Liver tissues were homogenized and extracted with a mixture of chloroform: methanol(2:1 v/v) containing 0.01% t-butylated hydroxytoluene as an antioxidant. The solvent fraction was isolated and evaporated to dryness under N2 and reconstituted in chloroform. The total phospholipids were separated by thin-layer chromatography on silica gel-H plates (Analtech Inc., Newark, Del.), and the fatty acid methyl esters were derived (Palombo et al., *Lipids* 29: 643–649 (1994)) and analyzed on a fused silica capillary column (100 m, 0.25 mm ID, 0.20 $\mu$m thickness; SP™-2560, Supelco Inc., Bellefonte, Pa.) using a gas chromatograph (5890 Series II) equipped with a mass selective detector (5971, Hewlett-Packard). The results were expressed as relative percent of identified fatty acids on a molar basis, using heptadecaenoic acid (17:0) as an internal standard.

Endotoxin-induced in vivo production of cytokines: A lethal dose ($LD_{50}/24$ hours=20 mg/kg) of lipopolysaccharide (LPS: E. col B55:05, Calbiochem. San Diego, Calif.) was injected intraperitonealy, and after 1 hour or 3 hours, the blood samples were collected from the inferior vena cava using 1 ml syringes rinsed with heparin. The plasma levels of TNF-$\alpha$, IL-6, IL-10 and IL-12 were determined according to the manufacturer's instructions using enzyme-linked immunosorbent assay kits (Biosource International, Camarrilo, Calif.).

Radioimmunoassays for Prostaglandin (PG)$E_2$: An aliquot of 50 $\mu$l plasma (in 1 ml PBS) was extracted twice with 2 ml ethyl acetate, and the solvent fractions were pooled and evaporated to dryness under $N_2$. The resultant extract was resuspended in PBS containing 0.1% gelatin, and the levels of $PGE_2$ were determined in a radioimmunoassay according to the procedures described elsewhere (Granstrom and Kindahl, *Adv Prost Throm Res* 119:119–210 (1978)). The polyclonal rabbit anti-$PGE_2$ was purchased from Perseptive Diagnostics (Cambridge, Mass.). According to the supplier's technical information, the $PGE_2$ antiserum has a 50% cross-reactivity with $PGE_1$. Therefore, the actual amounts of $PGE_2$ reported may represent $PGE_1$ (up to a maximum of 50%) if present, in the samples. No effort was made to correct for cross-reactivity with $PGE_1$.

Statistical analysis: The significance (P<0.05) in differences in the mean concentrations of cytokines, eicosanoids and fatty acids was determined using a student's t-test.

Results

Effects on the Membrane Fatty Acid Composition

The changes in the fatty acid composition (mean±s.d; mol. %) were determined in the liver membrane phospholipids from mice fed both the SO diets for 2 weeks (Table 1). The amounts of saturated, monounsaturated fatty acids and linoleic acid did not differ between the two groups.

However, the levels of 20:3ω6 (Dihomo-γ-linolenic acid) were significantly higher (p<0.02) in mice fed sesamol supplemented SO diet (1.6±0.1) compared to the control group (1.4±0.1). Similar data were obtained in mice fed for as short as 4 days (data not shown). Further, the levels of docosapentaenoic acid (Docosapentaenoic acid; 22:5ω6) were markedly lower in animals fed diets supplemented with sesamol (1.4±0.1) compared to those without (2.5±0.4). The A-5 desaturation index for ω6 fatty acids expressed as the ratio of Arachidonic acid/Dihomo-γ-linolenic acid was markedly lower (p<0.025) in animals fed diets supplemented with sesamol (15.6±1.5) compared to the control group (18.0±1.7).

Effects on the Production of Prostaglandin $E_2$

Figure 1B:
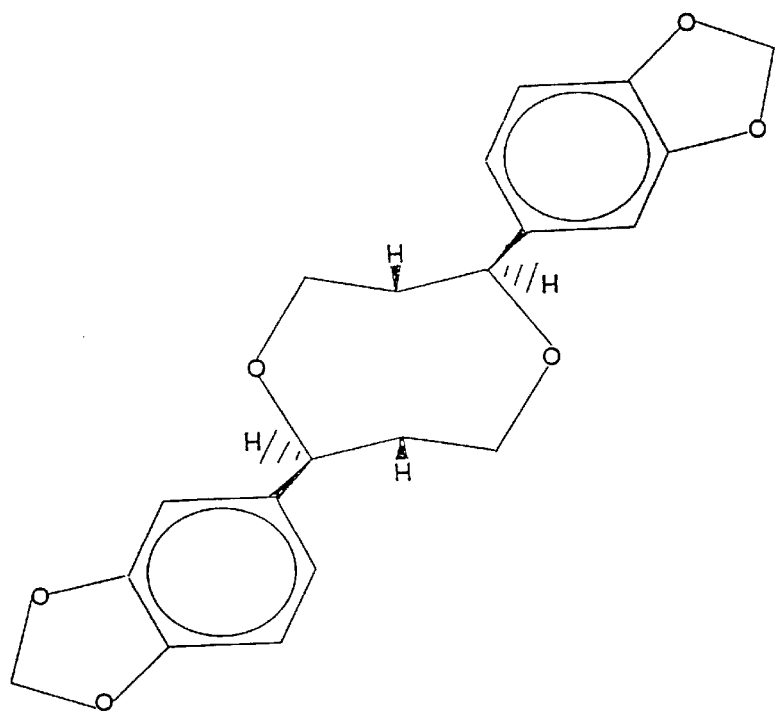

Accumulation of dihomo-γ-linolenic acid resulting from consumption of the sesamol diet (Table 2) could affect Arachidonic acid metabolism (Harrobin, *Rev Contem Pharmacolther* 1:1–45 (1990); Weaver and Holob, *Prog Food Nutr Sci* 12:111–150 (1988)). Therefore, the plasma levels of $PGE_2$ (mean±s.e.) were determined in response to LPS in animals fed both the SO diets (FIG. 1). The levels of $PGE_{1+2}$ (pg/ml) in mice fed sesamol supplemented SO diet (228±41) were significantly lower (P<0.05) compared to those maintained on SO alone (1,355±188).

Effects on the Production of TNF-α, IL-6, IL-10 and IL-12

Proinflammatory mediators such as $PGE_2$ (Zhong et al., *Immunol* 84:446–452 (1995); Pruimboom et al., *Immunol Lett* 41:255–260 (1994); I-Elger et al., *Int Arch Allergy Immunol* 107:383–384 (1995)) as well as other fatty acids (Carrick et al., *Shock* 2:421–426 (1994); Yacoob and Calder, Cell *Immunol* 163:120–128 (1995)) can influence the production of cytokines which mediate immune responses during infection and inflammation. In animals fed sesamol supplemented SO diet, the plasma levels of IL-6 (63±11 ng/ml) were significantly lower compared to those fed SO diet alone (143±22 ng/ml). The circulating levels of TNF-α, IL-10 and IL-12 did not differ markedly between the groups (Table 2). The weights of body, liver and of the spleen from mice fed sesamol supplemented diets were not significantly different from those fed SO diets. Further, the percent gain in body weights were almost identical in both the groups.

Equivalents

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of inhibiting Δ-5-desaturase activity in a mammal comprising administering to the mammal a composition comprising an effective amount of sesamol.

2. A method of inhibiting arachidonic acid metabolism in a mammal comprising administering to the mammal a composition comprising an effective amount of sesamol.

3. A method of inhibiting the level of $PGE_2$ in a mammal comprising administering to the mammal a composition comprising an effective amount of sesamol.

4. A method of inhibiting the activity of $PLA_2$ in a mammal comprising administering to the mammal a composition comprising an effective amount of sesamol.

5. A method of reducing IL-6 levels in a mammal comprising administering to the mammal a composition comprising an effective amount of sesamol.

* * * * *